United States Patent
Hatano et al.

(10) Patent No.: US 10,980,401 B2
(45) Date of Patent: Apr. 20, 2021

(54) ENDOSCOPE

(71) Applicant: OLYMPUS CORPORATION, Tokyo (JP)

(72) Inventors: Keisuke Hatano, Koganei (JP); Shun Nagasawa, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 390 days.

(21) Appl. No.: 16/038,442

(22) Filed: Jul. 18, 2018

(65) Prior Publication Data

US 2018/0317748 A1 Nov. 8, 2018

Related U.S. Application Data

(63) Continuation of application No. PCT/JP2016/077467, filed on Sep. 16, 2016.

(30) Foreign Application Priority Data

Jan. 20, 2016 (JP) .............................. JP2016-008629

(51) Int. Cl.
*A61B 1/00* (2006.01)
*A61B 1/005* (2006.01)
(Continued)

(52) U.S. Cl.
CPC .......... *A61B 1/0052* (2013.01); *A61B 1/0051* (2013.01); *A61B 1/00066* (2013.01); (Continued)

(58) Field of Classification Search
CPC ... A61B 1/0051; A61B 1/0052; A61B 1/0057; A61B 2034/742; A61B 1/00066; (Continued)

(56) References Cited

U.S. PATENT DOCUMENTS

2003/0006963 A1* 1/2003 Bredow ................. G05G 9/047
  345/161
2003/0137394 A1* 7/2003 Romero Herrera .. H01C 10/103
  338/32 H
(Continued)

FOREIGN PATENT DOCUMENTS

JP    S61-19341 A    1/1986
JP    S61-127031 U1  8/1986
(Continued)

OTHER PUBLICATIONS

International Search Report dated Dec. 13, 2016 issued in PCT/JP2016/077467.

*Primary Examiner* — Timothy J Neal
*Assistant Examiner* — Sung Ham
(74) *Attorney, Agent, or Firm* — Scully, Scott, Murphy & Presser, P.C.

(57) ABSTRACT

An endoscope includes a bending operation apparatus including: a rod-like shaft section that is standing perpendicularly from one surface of an operation section and capable of being tilted; and a cover member including a central section that is placed to externally cover the rod-like shaft section in a water tight manner, a peripheral section that closes in a water tight manner an opening portion in which the rod-like shaft section is disposed, and an intermediate section provided between the peripheral section and the central section, wherein the cover member of the bending operation apparatus includes a deformation restricting section that is a tubular section formed along a longitudinal axis of the rod-like shaft section and placed to externally cover an intermediate portion of the rod-like shaft section, and restricts outward expansion of the intermediate section.

5 Claims, 3 Drawing Sheets

(51) Int. Cl.
*A61B 1/01* (2006.01)
*G02B 23/24* (2006.01)

(52) U.S. Cl.
CPC ............ *A61B 1/01* (2013.01); *G02B 23/2476* (2013.01); *A61B 1/00131* (2013.01)

(58) Field of Classification Search
CPC .. A61B 1/01; A61B 1/00131; G02B 23/2476; G06F 3/033; G06F 3/0338; G05G 9/02; G05G 5/02; G05G 2009/04707; G05G 2009/04729
USPC .......................................... 345/161; 600/146
See application file for complete search history.

(56) References Cited

U.S. PATENT DOCUMENTS

| | | | | |
|---|---|---|---|---|
| 2004/0193014 | A1* | 9/2004 | Miyagi | A61B 1/00039 600/146 |
| 2004/0267093 | A1* | 12/2004 | Miyagi | A61B 1/00039 600/146 |
| 2009/0149709 | A1* | 6/2009 | Koitabashi | A61B 1/00149 600/131 |
| 2016/0192823 | A1* | 7/2016 | Yasunaga | A61B 1/0052 600/109 |
| 2017/0196435 | A1* | 7/2017 | Sato | G02B 23/2476 |

FOREIGN PATENT DOCUMENTS

| | | | | |
|---|---|---|---|---|
| JP | H02-81724 | A | | 3/1990 |
| JP | 2003-135385 | A | | 5/2003 |
| JP | 2003135385 | A * | 5/2003 | ........... A61B 1/0052 |
| JP | 2005-279119 | A * | 10/2005 | ............... A61B 1/00 |
| JP | 2011-105025 | A | | 6/2011 |

* cited by examiner

ENDOSCOPE

CROSS REFERENCE TO RELATED APPLICATION

This application is a continuation application of PCT/JP2016/077467 filed on Sep. 16, 2016 and claims benefit of Japanese Application No. 2016-008629 filed in Japan on Jan. 20, 2016, the entire contents of which are incorporated herein by this reference.

BACKGROUND OF THE INVENTION

1. Field of the Invention

The present invention relates to an endoscope including an operation section provided with a joystick that is operated when bending a bending portion.

2. Description of the Related Art

Endoscopes are used in the medical field or industrial field. An endoscope includes an elongated insertion section that is inserted into a living body or into a structure. An endoscope includes an insertion section provided with a bending portion.

For example, the bending portion is configured to be bent in two directions: up and down, or four directions: up, down, left and right. In an operation section located on a proximal end side of the insertion section, a bending operation apparatus, which is operated when bending the bending portion, is mounted.

Examples of the bending operation apparatus are a bending operation knob, a bending operation lever, and a joystick.

The bending portion is configured to be bent by a desired amount in a desired direction when a user, such as a doctor or an operator, operates the bending operation apparatus.

Each of the bending operation knob and the bending operation lever is integrally provided with a shaft body. The bending portion is bent by directly pulling and loosening a bending operation wire corresponding to a rotation amount of the shaft body, or the bending portion is bent by pulling and loosening the bending operation wire by outputting the rotation amount of the shaft body as a bending operation instruction signal to a control apparatus and driving a driving apparatus with a driving signal generated by the control apparatus.

On the other hand, the joystick includes a rod-like shaft section standing in a direction perpendicular to one surface of the operation section. The bending portion is bent by directly pulling and loosening a bending operation wire corresponding to a tilt amount that is a tilt direction and a tilt angle of the shaft section, or the bending portion is bent by pulling and loosening the bending operation wire by outputting the tilt amount of the shaft section as a bending operation instruction signal to a control apparatus and driving a driving apparatus with a driving signal generated by the control apparatus.

Japanese Patent Application Laid-Open Publication No. 2003-135385 discloses an endoscope apparatus including a bending lever, which is in a neutral state when the bending lever is self-standing, and capable of highly precisely bending a bending portion by operating the bending lever. A bending operation switch of the endoscope apparatus is composed of a joystick having a standing operation shaft, a bending lever having a shaft section integrally fixed to the operation shaft, and a bending boot having a boot portion formed of an elastic member.

The bending boot has an elastic force that brings the bending lever into a self-standing state, and also has an elastic force that causes the boot portion to be folded on a lever tilted side when the bending lever is tilted, and changes the boot portion to an extended state on the opposite side to the tilt.

For medical endoscopes, a leak test is performed to confirm the presence or absence of perforations and the like after surgery. In the leak test, the inside of the endoscope is caused to have a positive pressure by feeding air.

Then, in an endoscope with a joystick mounted in an operation section, as shown on the arrow YIA side in FIG. 1, a phenomenon occurs where a cover member 3 with an elastic force, which closes an opening portion 1a of an operation section 1 and externally covers a rod-like shaft section 2 led out to the outside, expands as indicated by the solid lines from an original state shown by the broken lines.

After confirming the presence or absence of perforations, when the pressure in an internal space of the endoscope is reduced to the same pressure as an external pressure, the cover member 3 expanded as shown by the solid lines returns to the original state.

SUMMARY OF THE INVENTION

An endoscope according to one embodiment of the present invention includes a bending operation apparatus including: a rod-like shaft section standing perpendicularly from one surface of an operation section and capable of being tilted, the operation section being provided on a proximal end side of an insertion section and capable of manipulating a bending angle of a bending portion provided in the insertion section; and a cover member including a central section that is placed to externally cover the rod-like shaft section in a water tight manner, a peripheral section that closes in a water tight manner an opening portion provided in the one surface, and an intermediate section provided between the peripheral section and the central section, the rod-like shaft section being disposed in the opening portion so that the rod-like shaft section is swingable, wherein the cover member of the bending operation apparatus includes a deformation restricting section that is a tubular section formed along a longitudinal axis of the rod-like shaft section and placed to externally cover an intermediate portion of the rod-like shaft section, and restricts outward expansion of the intermediate section.

An endoscope according to one embodiment of the present invention includes a bending operation apparatus including: a rod-like shaft section standing perpendicularly from one surface of an operation section and capable of being tilted, the operation section being provided on a proximal end side of an insertion section and capable of manipulating a bending angle of a bending portion provided in the insertion section; and a cover member including a central section that is placed to externally cover the rod-like shaft section in a water tight manner, a peripheral section that closes in a water tight manner an opening portion provided in the one surface, and an intermediate section provided between the peripheral section and the central section, the rod-like shaft section being disposed in the opening portion so that the rod-like shaft section is swingable, wherein the cover member of the bending operation apparatus includes a deformation restricting section that is a plurality of connection sections, each of the plurality of connection sections connecting a predetermined portion of the intermediate

DETAILED DESCRIPTION OF THE PREFERRED EMBODIMENT

Figure 1:
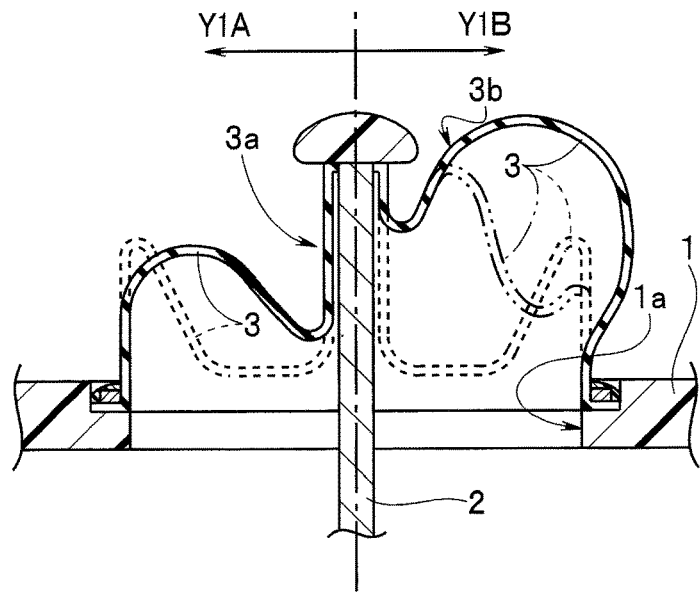
FIG. 1 is a diagram for explaining a state in which a cover member of a joystick is expanded and a state in which a tubular section of a cover member is raised up.

The present invention will be described with reference to the drawings.

Each of drawings used in the description below is a schematic illustration, and dimensional relationships, scales and the like of respective members may be changed for each component and shown in order to illustrate each component to such an extent that the component is recognizable on the drawings. Therefore, the present invention is not limited only to the forms shown in the drawings in respect of the number of components, shapes of the components, a size ratio of the components, and relative positional relationships among the respective components shown in the respective drawings.

Figure 2:
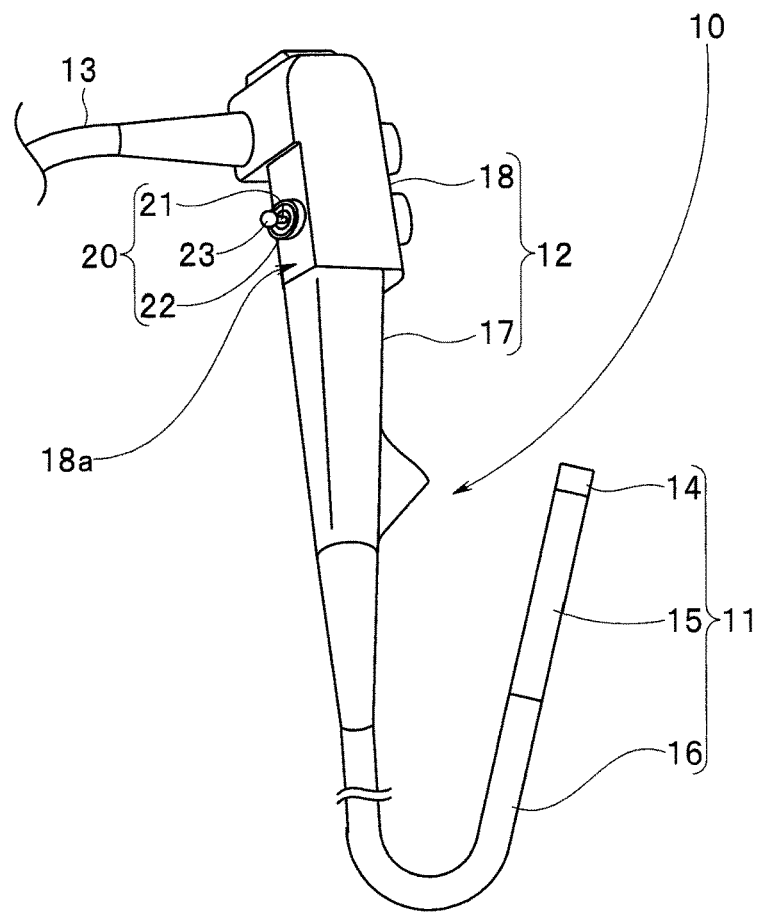
FIG. 2 is a diagram for explaining an endoscope.

As illustrated in FIG. 2, an endoscope 10 includes an insertion section 11, an operation section 12, and a universal cord 13. The operation section 12 is mounted on the proximal end side of the insertion section 11. The universal cord 13 extends from a side portion of the operation section 12.

The insertion section 11 includes a distal end portion 14, a bending portion 15, and a flexible tube portion 16 in this order from the distal end side. The bending portion 15 is bendable, for example, in up, down, right and left directions. An image pickup apparatus (not shown) having an image pickup device is incorporated in the distal end portion 14.

The operation section 12 includes a grasping portion 17 constituting the insertion section 11 side, which is one end side of the operation section 12, and an operation section main body 18 constituting the other end side away from the insertion section 11. An operation device 20 capable of being tilted is mounted on one surface 18a of the operation section main body 18.

The operation device 20 is a bending operation apparatus, and bends the bending portion 15, for example, by directly pulling a bending operation wire (not shown).

Figure 3A:
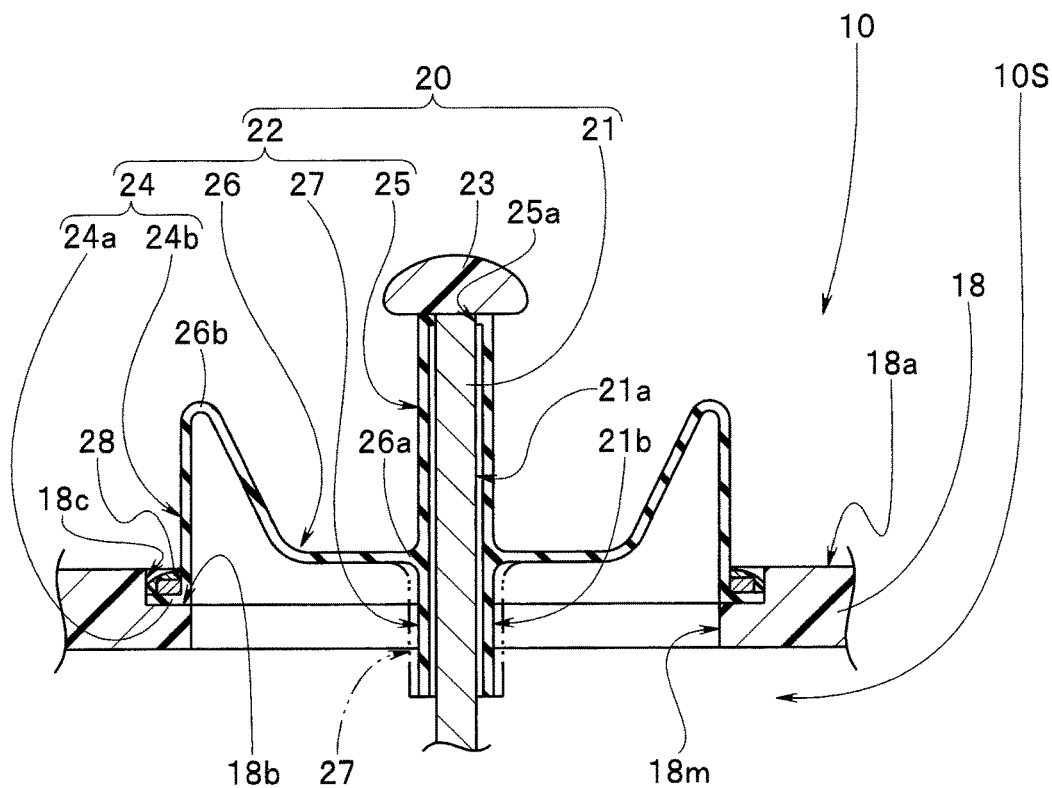
FIG. 3A is a diagram for explaining the cover member of the joystick mounted in an operation section.
Figure 3B:
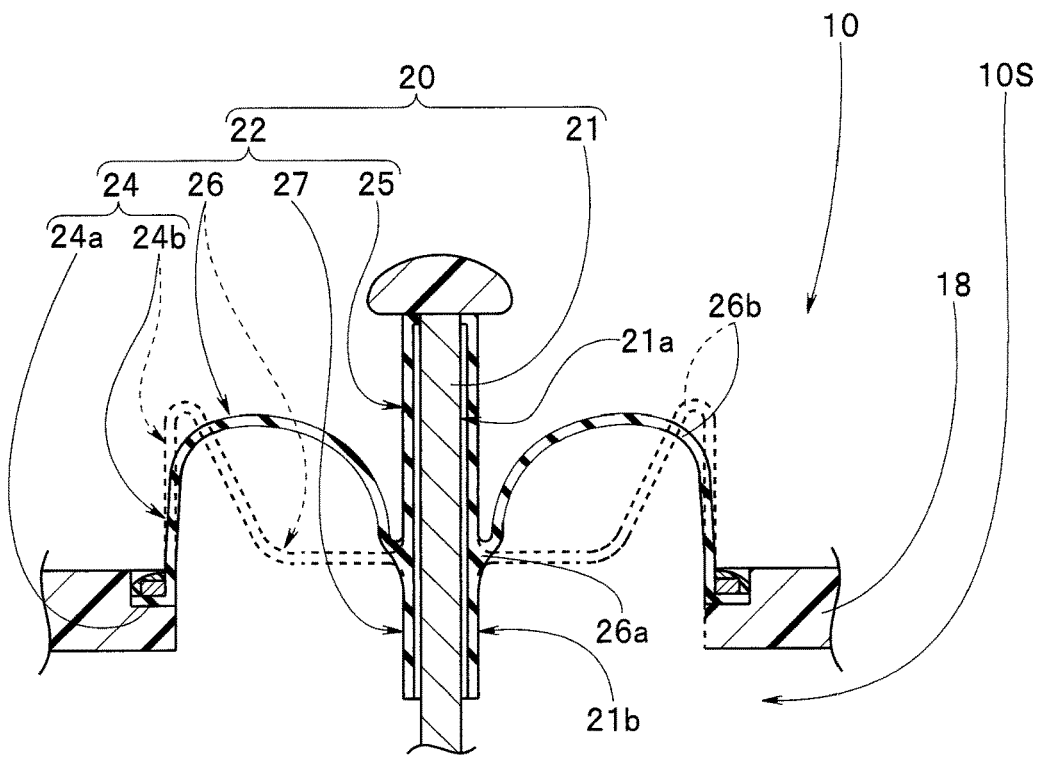
FIG. 3B is a diagram for explaining a state in which the cover member in FIG. 3A is expanded.

The operation device 20 illustrated in FIG. 2 and FIG. 3A is a so-called joystick including a rod-like shaft section (hereinafter abbreviated as the shaft section) 21 and a cover member 22 that is an elastic member. Reference sign 23 represents a finger contact section fixed integrally to an outer distal end that is one end of the shaft section 21 by screwing, adhesion, etc.

The shaft section 21 illustrated in FIG. 3A is capable of being tilted, and is led out of the main body by a predetermined amount from an opening portion 18m of the operation section main body 18. The opening portion 18m is circular or rectangular in shape, and the size of the opening is set so that the shaft section 21 has a predetermined tilt amount. The shaft section 21 is located at the center of the opening.

The cover member 22 includes a peripheral section 24, a central section 25, an intermediate section 26 and a deformation restricting section 27, and is formed in a predetermined shape.

The peripheral section 24 includes an edge portion 24a and a rising portion 24b. The edge portion 24a substantially coincides with the opening shape, is disposed on a bottom surface 18b of a recessed portion 18c provided around the opening of the opening portion 18m, and is integrally fixed with a fixing member and an adhesive 28 while ensuring water tightness. The rising portion 24b protrudes by a predetermined amount from the one surface 18a.

The central section 25 is a tubular section in which a through-hole 25a is Banned. The shaft section 21 is inserted and disposed in the through-hole 25a. The central section 25 is placed to externally cover, in a substantially close fitting manner, an outer peripheral surface of the outer distal end portion 21a of the shaft section 21.

The shaft section 21 is disposed in the through-hole 25a, and is fixed integrally to the central section 25 in a water tight manner with an adhesive (not shown) applied between the outer peripheral surface of the outer distal end portion 21a of the shaft section 21 and an inner peripheral surface of the through-hole 25a.

The intermediate section 26 has a center-side end portion 26a located at the lower end portion of the central section 25 on the lower side in the drawing and a peripheral-side end portion 26b located at the upper end portion of the rising portion 24b, and forms a region between the central section 25 and the peripheral section 24.

The intermediate section 26 enables the shaft section 21 to stand perpendicularly to the one surface 18a of the operation section main body 18 and be held at the center of the opening so that the shaft section 21 is capable of being tilted.

The deformation restricting section 27 is a tubular section disposed in a substantially close fitting manner around the outer peripheral surface of the shaft section 21 substantially similarly to the central section 25. The deformation restricting section 27 is disposed to externally cover a predetermined amount of an intermediate portion 21b that is located on the other end side of the shaft section 21 with respect to the central section 25. In other words, the deformation restricting section 27 is mounted so that the center-side end portion 26a is located between the central section 25 and the deformation restricting section 27.

Reference sign 10S is a space in the operation section main body 18, and is an endoscope internal space.

For the endoscope 10 including the operation device 20, a leak test is performed after surgery. At this time, the endoscope internal space 10S is changed to a positive pressure by feeding air. The cover member 22 of the operation device 20 mounted in the operation section 12 starts to be expanded against the elastic force.

In the present embodiment, the cover member 22 is provided with the tubular deformation restricting section 27. Therefore, moving the position of the center-side end portion 26a along the shaft section 21 and outward away from the shaft section 21 is difficult.

Accordingly, outward expansion of the intermediate section 26 of the cover member 22 is restricted, and, for example, the cover member 22 is expanded as indicated by the solid lines. As a result, the defect that the central section 25 is raised up to separate from the shaft section 21 with elastic deformation of the intermediate section 26 is resolved.

After completion of the leak test, the pressure in the endoscope internal space 10S is reduced to the same pressure as an external pressure. Then, the deformed intermediate section 26 is gradually deformed by the elastic force.

Thus, the cover member 22 is provided with the tubular deformation restricting section 27 disposed in a substantially close fitting manner around the outer peripheral surface of the shaft section 21 substantially similarly to the central section 25, and the center-side end portion 26a of the intermediate section 26 is disposed between the central section 25 and the deformation restricting section 27.

As a result, during the leak test, it is possible to prevent the position of the center-side end portion 26a of the intermediate section 26 from moving along the shaft section 21 and moving toward the outside of the shaft section 21.

Accordingly, outward expansion of the intermediate section 26 is restricted, and the defect that the central section 25 is raised up with deformation of the intermediate section 26 is resolved. When the pressure in the endoscope internal space 10S is reduced to the same pressure as the external pressure, the cover member 22 surely returns to the original state because of the elastic force.

Note that a thickness of the deformation restricting section 27 may be formed thicker than a thickness of the peripheral section 24 and a thickness of the central section 25 as shown by the long dashed double-dotted lines in FIG. 3A. By setting the thickness of the deformation restricting section 27 to be thicker, the elastic force of the deformation restricting section 27 is increased and the deformation restricting section 27 is disposed more securely in close contact with the outer peripheral surface of the shaft section 21.

As a result, it becomes harder to move the position of the center-side end portion 26a along the shaft section 21 and outward away from the shaft section 21, thereby resolving the defect that the central section 25 is raised up to separate from the shaft section 21 with elastic deformation of the intermediate section 26.

Other configuration and function of the cover member will be described with reference to FIG. 4A to FIG. 4C.

Figure 4A:
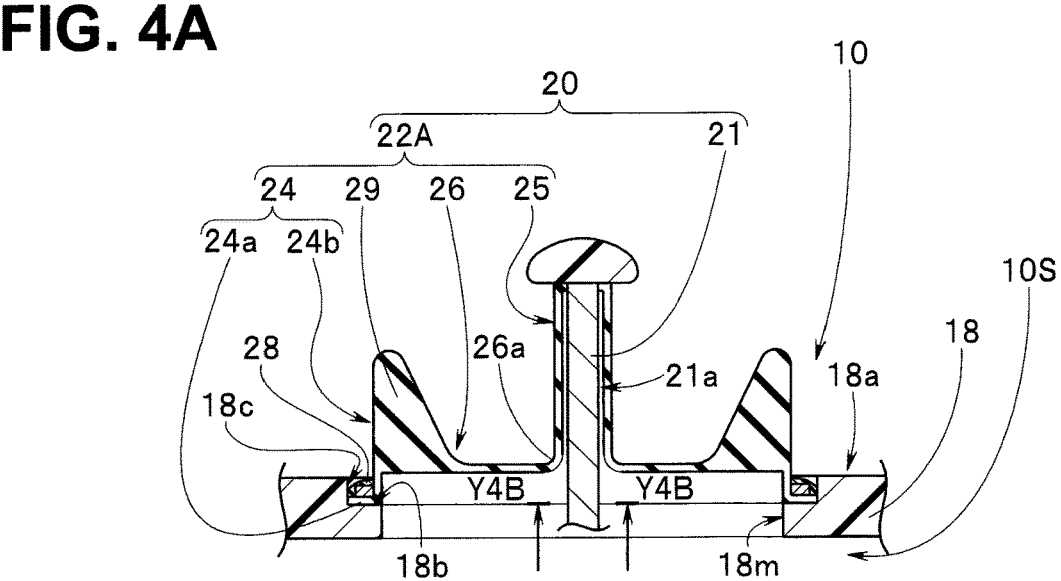
FIG. 4A is a diagram for explaining other configuration example of the cover member of the joystick.
Figure 4B:
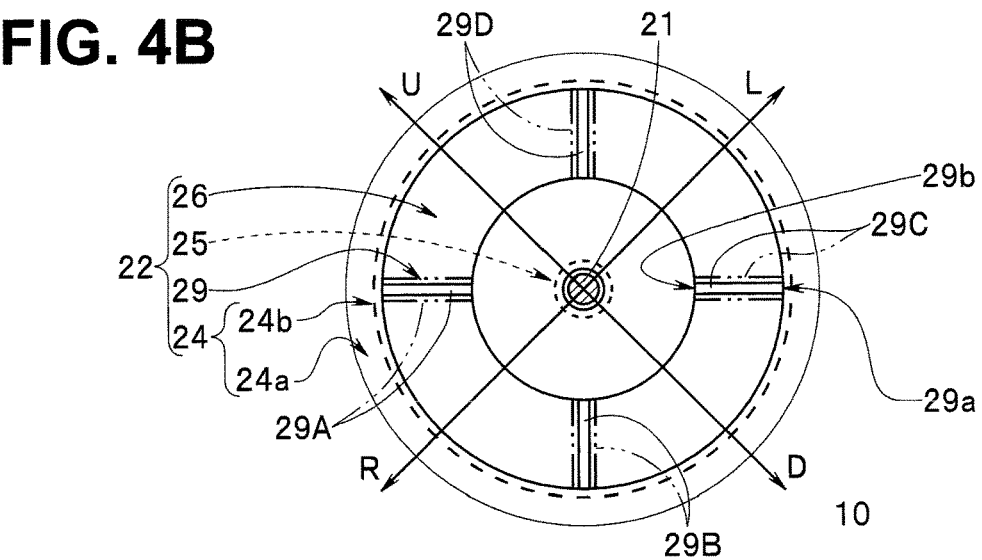
FIG. 4B is a bottom view of the cover member including a sectional view taken along Y4B-Y4B line in FIG. 4A.
Figure 4C:
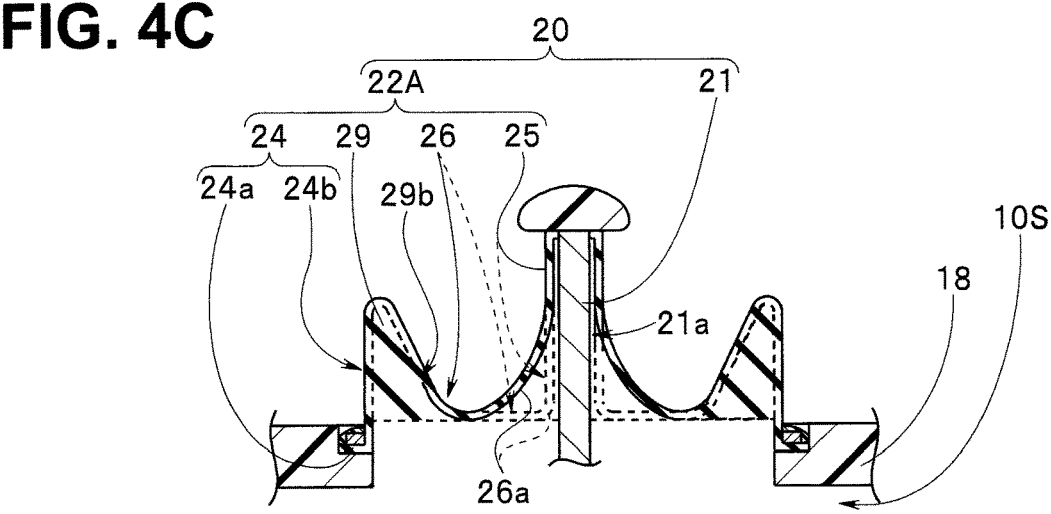
FIG. 4C is a diagram for explaining a state in which the cover member in FIG. 4A is expanded.

As illustrated in FIG. 4A and FIG. 4B, a cover member 22A constituting the operation device 20 of the present embodiment includes the peripheral section 24, the central section 25, the intermediate section 26 and a deformation restricting section 29, and is formed in a predetermined shape.

The deformation restricting section 29 is configured as a connection section that integrally connects the peripheral section 24 and the intermediate section 26 together. The deformation restricting section 29 is a plate-like section and has a thickness set to ensure a predetermined flexibility. For example, the deformation restricting section 29 is provided four in number, and the peripheral section 24 and the intermediate section 26 are integrally connected together by fixing a peripheral-side restricting portion 29a to a predetermined inner surface portion of the peripheral section 24 and fixing a center-side restricting portion 29b to a predetermined inner surface portion of the intermediate section 26.

In the present embodiment, the deformation restricting sections 29 are mounted radially at intervals of 90 degrees around the central axis of the shaft section 21.

More specifically, as illustrated in FIG. 4B, a first deformation restricting section 29A is positioned between an upward tilting direction U and a rightward tilting direction R of the shaft section 21; a second deformation restricting section 29B is positioned between the rightward tilting direction R and a downward tilting direction D of the shaft section 21; a third deformation restricting section 29C is positioned between the downward tilting direction D and a leftward tilting direction L of the shaft section 21; and a fourth deformation restricting section 29D is positioned between the leftward tilting direction L and the upward tilting direction U of the shaft section 21.

Note that although the four deformation restricting sections 29 are provided, the deformation restricting section 29 may be provided two, three, four or more in number. The center-side end portion 26a of the intermediate section 26 is located at the lower end portion of the central section 25, on the lower side in the drawing. Other components are the same as in the above-described embodiment, and the same members are labelled with the same reference signs and the descriptions are omitted.

Here, the function of the cover member 22A will be described.

In the leak test, as the inside of the endoscope internal space 10S is changed to a positive pressure, the cover member 22A starts to be expanded against the elastic force. In the present embodiment, the cover member 22A is provided with the deformation restricting section 29 in the form of a plate. Therefore, in the present embodiment, it is possible to prevent the position of the center-side restricting portion 29b from being moved largely.

Accordingly, outward expansion of the intermediate section 26 of the cover member 22A is restricted, and, for example, the cover member 22A is expanded as indicated by the solid lines. At this time, with the expansion, as shown in the drawing, there is a case that the cover member 22A is deformed into a state in which the lower end portion side of the central section 25 is slightly separated from the shaft section 21.

After completion of the leak test, the pressure in the endoscope internal space 10S is reduced to the same pressure as the external pressure. Then, the deformed intermediate section 26 and the central section 25 are gradually deformed by the elastic force.

Thus, the cover member 22A is provided with a plurality of plate-like deformation restricting sections 29 that connect the inner surface of the peripheral section 24 and the inner surface of the intermediate section 26 together in a predetermined state. As a result, during the leak test, it is possible to prevent movement of the position of the inner surface of the intermediate section 26 to which the center-side restricting portion 29b is fixed.

Accordingly, outward expansion of the intermediate section 26 is restricted, and the defect that the central section 25 is raised up with deformation of the intermediate section 26 is resolved. When the pressure in the endoscope internal space 10S is reduced to the same pressure as the external pressure, the cover member 22A surely returns to the original state because of the elastic force.

Note that a thickness of the deformation restricting sections 29A, 29B, 29C and 29D illustrated in FIG. 4B which are the deformation restricting sections 29 may be formed thicker than the thickness of the peripheral section 24 and the thickness of the central section 25 as indicated by the long dashed double-dotted lines. By setting the thickness of the deformation restricting sections 29A, 29B, 29C and 29D to be thicker, the elastic force is increased and makes it harder to move the position of the inner surface of the intermediate section 26 to which the center-side restricting portion 29b is fixed.

In short, with the elastic forces of the deformation restricting sections 29A, 29B, 29C and 29D, the defect that the central section 25 is raised up is resolved, and it is possible to cause the cover member 22A to quickly and surely return to the original state.

The present invention is not limited to the above-described embodiment, and various modifications and applications can be made without departing from the gist of the invention.

In the present invention, with an operation of tilting the operation device, the bending operation wire is directly pulled, and the bending portion provided in the insertion section of the endoscope is bent. However, the endoscope may be configured with a bending portion that is bent as the bending operation wire is pulled and loosen by a driving apparatus driven by a driving signal which is generated based on a signal outputted to a control apparatus by an operation of tilting the operation device.

Further, the endoscope is a so-called electronic endoscope incorporating an image pickup apparatus in the distal end portion 14. However, the endoscope may be a so-called optical endoscope including an optical fiber bundle that transmits an optical image, the optical fiber bundle being inserted into the insertion section.

According to the present invention, it is possible to realize an endoscope including a bending operation apparatus that prevents the cover member from being raised up beyond an elastic range when the internal space of the endoscope is brought to a positive pressure for a leak test, and allows the cover member to surely return to the original state when the pressure in the internal space of the endoscope is reduced to the same pressure as the external pressure.

What is claimed is:

1. An endoscope comprising:
    a bending operation apparatus, the bending operation apparatus comprising:
        a shaft standing perpendicularly from a surface of an operation section, the shaft being configured to tilt, the operation section being provided on a proximal end side of an insertion section and configured to manipulate a bending angle of a bending portion provided in the insertion section; and
    a cover comprising:
        a central section configured to externally cover the shaft in a water tight manner,
        a peripheral section that closes in a water tight manner an opening provided in the surface,
        an intermediate section provided between the peripheral section and the central section, the shaft being disposed in the opening portion so that the shaft is swingable, and
        a deformation restricting section configured to restrict an outward expansion of the intermediate section, the deformation restricting section having a tubular shape formed along a longitudinal axis of the shaft to externally cover the shaft,
        wherein a first end of the intermediate section is connected at a transition between an upper end of the deformation restricting section and a lower end of the central section; and
        at least a portion of the deformation restricting section is located within the opening.

2. The endoscope according to claim 1, wherein a thickness of the deformation restricting section is thicker than a thickness of the peripheral section and a thickness of the central section.

3. The endoscope according to claim 1, wherein the central section, the peripheral section, the intermediate section, and the deformation restricting section are integrally formed.

4. The endoscope according to claim 3, wherein the central section, the peripheral section, the intermediate section, and the deformation restricting section are made of a same material.

5. The endoscope according to claim 1, wherein
    the peripheral section comprises a rising portion protruding from the opening portion,
    a second end of the intermediate section is connected to the peripheral section, and
    the second end of the intermediate portion is located more distally, relative to the shaft, than the first end of the intermediate portion.

* * * * *